United States Patent [19]
Schramm

[11] 3,937,225
[45] Feb. 10, 1976

[54] ELECTRODE ADAPTED FOR IMPLANTATION

[75] Inventor: Georg Schramm, Cologne, Germany

[73] Assignee: Siemens Aktiengesellschaft, Erlangen, Germany

[22] Filed: Feb. 4, 1974

[21] Appl. No.: 439,607

[30] Foreign Application Priority Data
Feb. 2, 1973  Germany............................ 2305262

[52] U.S. Cl. .................... 128/418; 128/419 P
[51] Int. Cl.² ........................................... A61N 1/04
[58] Field of Search .... 128/349 B, 404, 418, 419 P, 128/2.06 E, 2.1 F, DIG. 4

[56] References Cited
UNITED STATES PATENTS

| | | | |
|---|---|---|---|
| 3,435,826 | 4/1969 | Fogarty | 128/349 B |
| 3,437,091 | 4/1969 | Jerushalmi et al. | 128/419 P |
| 3,680,544 | 8/1972 | Shinnick et al. | 128/419 P |
| 3,707,960 | 1/1973 | Freed | 128/2.06 E |
| 3,746,003 | 7/1973 | Blake et al. | 128/349 B |
| 3,754,555 | 8/1973 | Schmitt | 128/419 P |
| 3,837,347 | 9/1974 | Tower | 128/419 P |

OTHER PUBLICATIONS
Ganz et al., "Medical Instrumentation," Vol. 6, No. 2, Mar.–Apr, 1972, p. 167.

*Primary Examiner*—William E. Kamm
*Attorney, Agent, or Firm*—Haseltine, Lake & Waters

[57] ABSTRACT

An electrode adapted for implantation for effecting the intracardial stimulation of a heart through the intermediary of an implanted heart pacemaker. The electrode, without the need for a barb on the electrode head, may be securely placed within the heart, and in which it is also afforded that, as required, a safe relocation thereof may be carried out in which no injury is occasioned of the muscle tissues encompassing the electrode head. The foregoing includes means for the anchoring of the electrode head, comprising a receptacle of a variable volume which is connected with the electrode in a region proximate to the electrode head, and with the receptacle incorporating at least partly elastic walls and a closable connecting conduit for the filling of the receptacle.

14 Claims, 3 Drawing Figures

ELECTRODE ADAPTED FOR IMPLANTATION

FIELD OF THE INVENTION

The present invention relates to an electrode adapted for implantation for effecting the intracardial stimulation of a heart through the intermediary of an implanted heart pacemaker, wherein the electrode comprises an electrical conductor provided with an electrical insulation, having an uninsulated generally cylindrical electrode head for the transmission of the stimulating impulse to the heart through the inserted electrode, at the end of the conductor which is proximate to the heart, and being provided at the end thereof remote from the heart with an electrical connector element for the heart pacemaker, as well as means for effecting the anchoring of the electrode head in the heart.

DISCUSSION OF THE PRIOR ART

Electrodes which do not incorporate for the anchoring of the electrode heads in the heart are subject to the disadvantage in that, due to heart contractions and as a consequence of the blood flow in the heart, there are occasioned undesirable dislocations of the electrode head, which may result in serious consequences for the patient. Heretofore, for this purpose the contacts of the implantable electrodes which are proximate the heart have been provided with barbs or hooks which are hooked to the inside of the heart muscle. In that manner there may be attained the object that the electrode remains relatively secure at the location into which it is hooked.

However, in actual practice it has been ascertained that repositioning of the electrode is, relatively frequently, either required or desirable. In that regard, and also for inadvertent dislocations, the barbs on the electrode heads have been found to be disturbing, since they possess the inherent danger that, upon a positioned change of the electrode head, the heart tissues may be injured by the barbs. Furthermore, during the course of time, it may also be possible that damages may occur through penetration or perforation.

SUMMARY OF THE INVENTION

Accordingly, it is a primary object of the present invention to provide an electrode which, without the need for a barb on the electrode head, may be securely placed within the heart, and in which it is also afforded that, as required, a safe relocation thereof may be carried out in which no injury is occasioned of the muscle tissues encompassing the electrode head.

The foregoing object is inventively resolved in that, as a means for the anchoring of the electrode head, there is provided a receptacle of a variable volume which is connected with the electrode in a region proximate to the electrode head, and with the receptacle incorporating at least partly elastic walls and a closable connecting conduit for the filling of the receptacle.

In an advantageous embodiment of the invention, the receptacle is formed of an elastic material hose section. It is preferable that the connecting conduit be so constructed and located, as to lie in parallel with the extended electrical conductor. The foregoing may be achieved in a particularly elegant and simple manner when the connecting conduit is realized through a passageway extending in the insulation. Within the concept of the invention, the end of the passageway adjacent the electrode head is closed off, and preferably in a manner in which that the passageway walls converge conically. In a particularly technically simple constructional embodiment, the passageway possesses a side aperture in the region of the elastic hose section, and preferably in the central section of the latter. The hose section is preferably so constructed and dimensioned as to be expandable in a balloon-like manner under the effects of a filling medium. In actual practice it has been found applicable that for the elastic portion of the receptacle, and preferably also for the insulation, there be employed a material which is known by the designation of a silicon rubber. The receptacle, moreover, is so constructed and dimensioned as to be able to receive a filling quantity of at least 0.3 cm$^3$, and preferably 0.5 cm$^3$. The filling material may, preferably be constituted of a liquid. The diameter of the filled balloon should preferably lie in the range of between 5 millimeters and 12 millimeters, and particularly has a preferred diameter of 8 millimeters. In that connection, when not filled, the hose lies, due to the effect of its elasticity, close to the insulation so that the volume of the receptacle is extremely small, or practically zero.

After the insertion of the electrode below the pumping or operating chamber of the heart, by filling the receptacle with a liquid, the electrode head is pressed against the endocard, and it is thereby attained that, notwithstanding the movements of the heart muscles, the electrode remains securely fastened although the head is not provided with a barb or hook, but is formed in an essentially cylindrical configuration. When a repositioning of the electrode becomes necessary, then the only requirement is to allow the liquid to flow out of the receptacle, which follows through the effect of the elasticity of the receptacle (or through a dosed aspiration). Thereafter, the repositioning may be carried out and through renewed filling of the receptacle, the electrode may then be fixed in its new position. The filled receptacle also prevents penetration or introduction of the electrode head into, for example, the chamber wall of the heart.

The purpose of application of the inventive electrode, and its specialized construction, basically distinguish over the socalled passed-through endocard electrodes, whose electrode ends remote from the heart are not provided with a connection for an implanted pacemaker but which incorporate, for example, contact pins for external pulse generators, or connect to an electrocardiograph for the recording of the internal EKG. Such electrodes, which are adapted for short-term stimulation are, for example, inserted through an arm or shoulder vein, and then moved along with their head until conveyed into the heart. The forward movement of the electrode may thereby be rendered somewhat more easy in that, immediately behind the electrode head, a receptacle is expanded balloon-like, so as to elevate the flow resistance of the electrode in the vein, and the blood flowing back towards the heart takes the balloon along (and concurrently the electrode). As soon as the electrode head arrives at the desired location in the heart, it is emptied. The inventive purpose and the inventive use are also not provided for in the known through-passed endocard electrodes.

BRIEF DESCRIPTION OF THE DRAWING

In the following detailed description there is illustrated an exemplary embodiment of the invention taken in conjunction with the accompanying drawing, in which.

DETAILED DESCRIPTION

Figure 1:
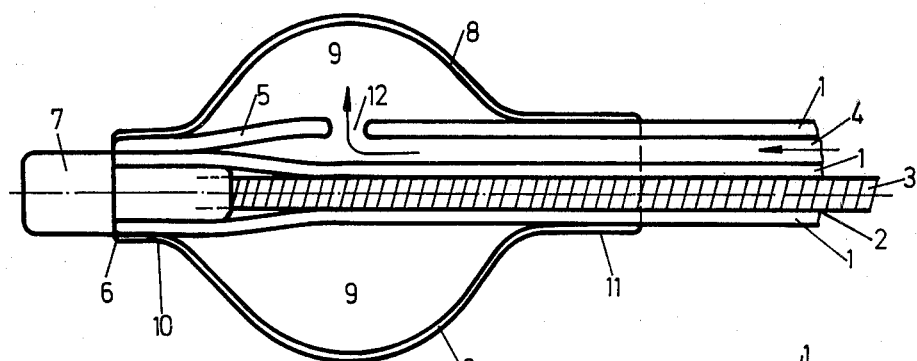
FIG. 1 illustrates, in an enlarged scale, the end of an endocard electrode which is proximate the heart.

Referring now in detail to the drawing, in FIG. 1 there is illustrated a dual-passageway hose 1 which is formed of a (electrically insulating) silicon rubber. One of the passageways 2 is adapted to receive an electrical conductor 3, while passageway 4, which extends parallel with passageway 2, serves for the introduction of a liquid (for example, a common salt or saline solution). The passageway 4 is terminated in that its walls converge conically at point 5 and combine with the remaining silicon rubber insulation. From the thus formed end portion 6 of the insulation, there projects a cylindrically-shaped electrode head 7, which is connected with the conductor 3. The referred to end portion of the electrode is encompassed by an elastic hose section 8 which, together with the dual-passageway hose 1, forms a receptacle 9 of a variable volume, and which has a length of approximately 12 mm. In its at-rest position, the hose section 8 lies closely against the dual-passageway hose 1 so that the receptacle exhibits practically no volume. At both of its ends 10 and 11, the hose section 8 is sealingly connected with the electrode components (head 7, as well as hose 1). The passageway 4, in the central region of the hose section 8, has a sidewall aperture 12 through the intermediary of which there may be carried out the filling of the receptacle. In the illustrated representation, the hose section 8 is shown expanded into a balloon form through the filling thereof with a liquid. The size of the expansion may be coordinated with the particular physiological circumstances, and normally measures approximately 8 mm in diameter.

Figure 2:
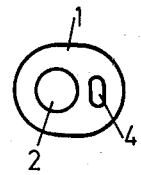
FIG. 2 is a sectional view, in an enlarged scale, through the insulating hose for the electrode of FIG. 1, and which is formed as a hose having dual-passageways.

In FIG. 2, the same components as in FIG. 1 are designated with identical reference numerals.

Figure 3:
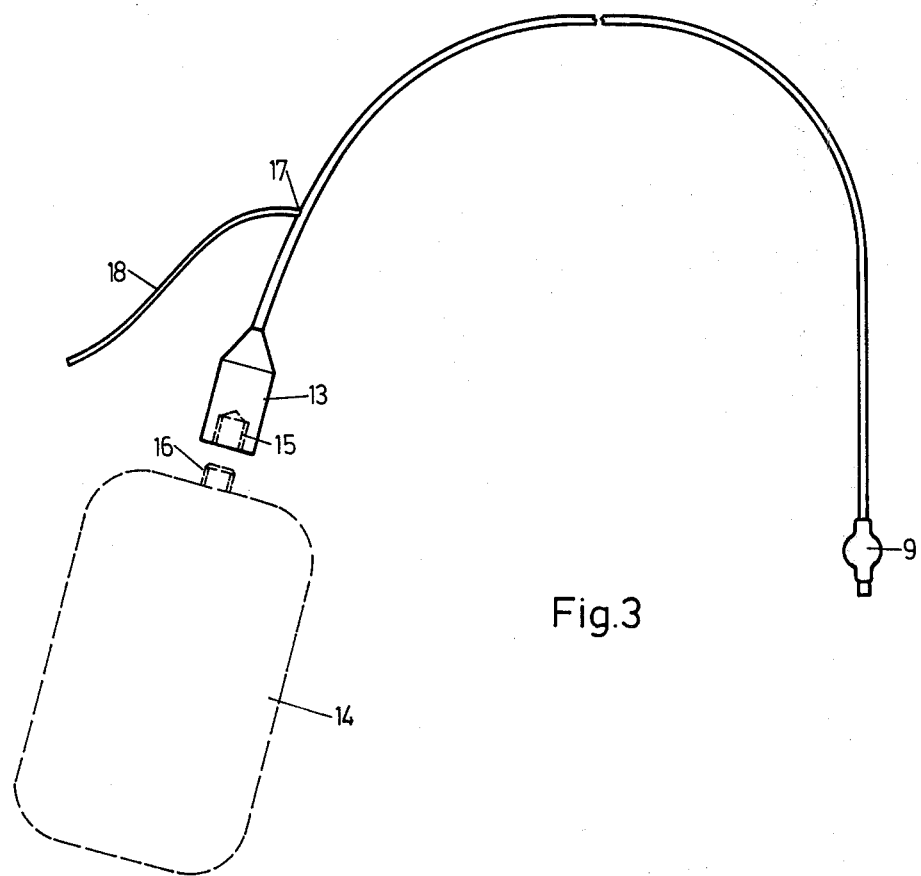
FIG. 3 is a general view of an assembled electrode adapted for implantation.

From FIG. 3, there may be ascertained a connecting member 13 which is at a location remote from the heart, and through which the electrode may be connected with a chain-dot illustrated implantable heart pacemaker 14. For this purpose, the connecting member 13 may be provided with an internal or female thread 15, and the pacemaker 14 with a portion having a complementary external or male thread 16. The dual-passageway hose includes an aperture 17 communicating with passageway 4, and in which there is inserted a thin hose section 18 through which the receptacle 9 may be filled, for example, by means of a syringe. Through knotting, this hose section may be easily closed off.

The described electrode may be formed by relatively simple components, and has been found widely applicable in practice. The material for the hose section there may be employed silicon rubber, which possesses extremely good long-term usage properties for the intended purpose.

While there has been shown what is considered to be the preferred embodiment of the invention, it will be obvious that modifications may be made which come within the scope of the disclosure of the specification.

What is claimed is:

1. In an electrode for use in effecting the intracardial stimulation of a heart through an implanted heart pacemaker, said electrode comprising an elongate electrical conductor; an electrical insulation encompassing said conductor, an uninsulated generally cylindrical electrode head being connected to said conductor at one end thereof for transmission of stimulating impulses to the heart from the electrode and being mounted on the proximal end of said insulation, means on said electrode for anchoring said electrode head in the heart, and electrical connector means at the distal end of the conductor adapted for connection to a pacemaker, the improvement comprising; said electrode including a continuous elongate hose forming said electrical insulation for said conductor, said hose having first and second parallel longitudinal passageways, said electrical conductor being positioned in the first of said passageways; said electrode head anchoring means including a volumetrically variable receptacle having at least partly elastic wall portions, said receptacle being connected to said electrode in a region adjacent to said electrode head, and said second passageway forming a closable connecting conduit means communicating with said receptacle for filling the latter with a receptacle-expanding medium.

2. An electrode as claimed in claim 1, said receptacle being formed of an elastic material hose portion, said hose portion sealingly engaging said electrical insulation at its ends.

3. An electrode as claimed in claim 2, said hose portion at one end thereof having a portion sealingly encompassing the electrical insulation in proximate axially spaced relationship to said electrode head and at the other end thereof having a portion sealingly encompassing said electrode head.

4. An electrode as claimed in claim 2, said hose portion being constructed to expand into a balloon-like configuration upon said medium being filled into said receptacle.

5. An electrode as claimed in claim 4, said balloon-like expanded receptacle having an expanded diameter in the range of 5 to 12 mm.

6. An electrode as claimed in claim 5, said balloon-like expanded receptacle having an expanded diameter of 8 mm.

7. An electrode as claimed in claim 1, said connecting conduit means extending in parallel with the longitudinally extended electrical conductor.

8. An electrode as claimed in claim 1, said second passageway having a side aperture communicating with the exterior of said elongate hose and the interior of said receptacle.

9. An electrode as claimed in claim 1, said receptacle having at least the elastic wall portions thereof formed of silicon rubber.

10. An electrode as claimed in claim 1, said electrical insulation being formed of silicon rubber.

11. An electrode as claimed in claim 1, said receptacle in the volumetrically expanded condition thereof being adapted to receive a quantity of filling medium in the range of 0.1 to 0.5 $cm^3$.

12. An electrode as claimed in claim 1, said receptacle extending along said electrode for a distance about 5 to 12 mm.

13. An electrode as claimed in claim 12, said receptacle having a length of 8 mm.

14. An electrode as claimed in claim 1, said receptacle having elastically deformable wall portions closely contacting the non-elastic walls thereof in the emptied condition of the receptacle.

* * * * *